US010403403B2

(12) United States Patent
Fung et al.

(10) Patent No.: US 10,403,403 B2
(45) Date of Patent: Sep. 3, 2019

(54) ADAPTIVE MEDICAL DOCUMENTATION SYSTEM

(71) Applicant: Cerner Innovation, Inc., Kansas City, KS (US)

(72) Inventors: Glenn Fung, Madison, WI (US); Balaji Krishnapuram, King of Prussia, PA (US); Faisal Farooq, Norristown, PA (US); Shipeng Yu, Exton, PA (US); Joseph Marcus Overhage, Zionsville, IN (US); John Haley, Chester Springs, PA (US); Jan DeHaan, Hawley, PA (US); Vikram Anand, Downington, PA (US)

(73) Assignee: Cerner Innovation, Inc., Kansas City, KS (US)

(*) Notice: Subject to any disclaimer, the term of this patent is extended or adjusted under 35 U.S.C. 154(b) by 1004 days.

(21) Appl. No.: 14/039,125

(22) Filed: Sep. 27, 2013

(65) Prior Publication Data
US 2014/0095206 A1 Apr. 3, 2014

Related U.S. Application Data

(60) Provisional application No. 61/707,147, filed on Sep. 28, 2012.

(51) Int. Cl.
*G06F 19/00* (2018.01)
*G16H 50/30* (2018.01)
*G16H 10/60* (2018.01)
*G16H 50/20* (2018.01)

(52) U.S. Cl.
CPC .............. *G16H 50/30* (2018.01); *G06F 19/00* (2013.01); *G16H 10/60* (2018.01); *G16H 50/20* (2018.01)

(58) Field of Classification Search
CPC ......... G06Q 10/00; G06Q 50/22; G06Q 50/24
USPC ......................................................... 705/2, 3
See application file for complete search history.

(56) References Cited

U.S. PATENT DOCUMENTS

| 5,222,236 A | 6/1993 | Potash et al. |
| 5,522,066 A | 5/1996 | Lu |
| 5,619,708 A | 4/1997 | Ho |
| 5,704,029 A | 12/1997 | Wright, Jr. |
| 5,737,539 A | 4/1998 | Edelson et al. |
| 5,764,992 A | 6/1998 | Kullick et al. |

(Continued)

FOREIGN PATENT DOCUMENTS

WO 2001069444 9/2001

OTHER PUBLICATIONS

Muench, S., "Building Oracle XML Applications", O'Reilly & Associates, 2000, cover, copyright page and pp. 284-309, 375-387 and 433-499.

(Continued)

*Primary Examiner* — Mark Holcomb
(74) *Attorney, Agent, or Firm* — Shook Hardy & Bacon LLP

(57) ABSTRACT

Adaptive medical data collection for medical entities may involve triggering an analysis of electronic records in response to information input into an Electronic Medical Record (EMR) of a patient. Determining a potential condition for the patient based on the analysis. Identifying additional information indicated as relevant to the potential condition of the patient, and generating a request for the identified additional information.

17 Claims, 4 Drawing Sheets

(56) References Cited

U.S. PATENT DOCUMENTS

| | | | |
|---|---|---|---|
| 5,857,967 | A | 1/1999 | Frid et al. |
| 5,859,972 | A | 1/1999 | Subramaniam et al. |
| 6,065,026 | A | 5/2000 | Cornelia et al. |
| 6,084,585 | A | 7/2000 | Kraft et al. |
| 6,119,130 | A | 9/2000 | Nguyen et al. |
| 6,119,137 | A | 9/2000 | Smith et al. |
| 6,128,661 | A | 10/2000 | Flanagin et al. |
| 6,151,643 | A | 11/2000 | Cheng et al. |
| 6,195,667 | B1 | 2/2001 | Duga et al. |
| 6,199,115 | B1 | 3/2001 | DiRienzo |
| 6,209,004 | B1 | 3/2001 | Taylor |
| 6,345,278 | B1 | 2/2002 | Hitchcock et al. |
| 6,473,892 | B1 | 10/2002 | Porter |
| 6,476,828 | B1 | 11/2002 | Burkett et al. |
| 6,498,657 | B1 | 12/2002 | Kuntz et al. |
| 6,606,604 | B1 | 8/2003 | Dutta |
| 6,816,630 | B1 | 11/2004 | Werth et al. |
| 8,065,655 | B1 | 11/2011 | Deo et al. |
| 8,150,711 | B2 | 4/2012 | Kelly et al. |
| 2002/0055945 | A1 | 5/2002 | Endress et al. |
| 2002/0169764 | A1 | 11/2002 | Kincaid et al. |
| 2002/0194028 | A1 | 12/2002 | Johnston et al. |
| 2003/0023626 | A1 | 1/2003 | Bretti |
| 2003/0037069 | A1 | 2/2003 | Davison |
| 2003/0074222 | A1 | 4/2003 | Rosow |
| 2003/0088438 | A1 | 5/2003 | Maughan et al. |
| 2003/0088565 | A1* | 5/2003 | Walter et al. ............ 707/6 |
| 2003/0101238 | A1 | 5/2003 | Davison |
| 2003/0120514 | A1* | 6/2003 | Rao et al. ............ 705/2 |
| 2003/0233257 | A1 | 12/2003 | Matian et al. |
| 2004/0153965 | A1* | 8/2004 | O'Rourke ............ 715/505 |
| 2005/0234740 | A1* | 10/2005 | Krishnan ......... G06Q 10/06398 705/2 |
| 2006/0178908 | A1 | 8/2006 | Rappaport |
| 2007/0130206 | A1 | 6/2007 | Zhou et al. |
| 2007/0239043 | A1* | 10/2007 | Patel et al. ............ 600/508 |
| 2008/0059391 | A1* | 3/2008 | Rosales et al. ............ 706/12 |
| 2008/0201280 | A1* | 8/2008 | Martin et al. ............ 706/12 |
| 2008/0269571 | A1* | 10/2008 | Brown et al. ............ 600/300 |
| 2010/0131883 | A1 | 5/2010 | Linthicum et al. |
| 2010/0235330 | A1 | 9/2010 | Reiner |
| 2011/0184954 | A1 | 7/2011 | Nelson |
| 2011/0202486 | A1* | 8/2011 | Fung et al. ............ 706/12 |
| 2011/0257988 | A1* | 10/2011 | Denekamp et al. ............ 705/2 |
| 2012/0078062 | A1* | 3/2012 | Bagchi et al. ............ 600/300 |
| 2013/0304487 | A1 | 11/2013 | Kuwayama |

OTHER PUBLICATIONS

Marchal, B., "Applied XML Solutions, The Authoritative Solution", Sam's, 2000, cover, copyright page, and pp. 71-194, 208-214, and 329-499.
ProLaw Document Management http://www.prolaw.com/document.html.
Report Lab http://www.reportlab.com.
Inventive Designers http://www.inventivedesigners.com.
"The Future of medicine is in your hands", PALM Healthcare Solutions http://www.palm.com/solutions/healthcare, 5 pages.
Health Data Management, "Is the Future in the Palm of Your Hand?", Jan. 2002, www.healthdatamanagement.com.
Virtual Medical Worlds, "Four top hospitals standardise on PatientKeeper's Mobilizer Platform to make physicians mobile and wireless", website http://www.hoise.com/vmw/02/articles/vmw/LV-VM-03-02-23.html.
Courter, et al., "Mastering Microsoft Office 2000 Professional Edition", 1999, Sybex, Inc., pp. 225-237.
Final Office Action dated Oct. 22, 2015 in U.S. Appl. No. 14/166,102, 32 pages.

* cited by examiner

ADAPTIVE MEDICAL DOCUMENTATION SYSTEM

RELATED APPLICATIONS

The present patent document claims the benefit of the filing date under 35 U.S.C. § 119(e) of Provisional U.S. Patent Application Ser. No. 61/707,147, filed Sep. 28, 2012, which is hereby incorporated by reference.

FIELD OF THE INVENTION

The present embodiments relate to medical documentation customization. Specifically, the present embodiments relate to automatic medical documentation adaptation for predicted or probable patient medical conditions.

BACKGROUND

Medical entities acquire and store significant amounts of patient medical information for diagnosis and tracking purposes. Historically, this information was acquired using paper forms, filled out by patients or medical entity personnel. Also, medical entity personnel would need to know specifically which forms to provide to patients depending on the specific medical history, current condition of the patient, and any other information that may be relevant to medical care of the patient. Often, the multitude of forms actually used for a given patient would request the same information multiple times. These forms may then be stored in a paper file, for future references by medical entity personnel.

Electronic Medical Records (EMR) have become a standard storage technique for medical and health records for patients of medical practitioners and medical entities. EMRs contain a considerable amount of medical data for specific patients, from various sources and in various formats. Collections of EMRs for medical facilities provide medical records and history for most, if not all, patients in a medical entity.

The entry of data into an EMR, however, may still be a very complex issue involving the manual selection of proper electronic forms for particular patients. Medical facilities and medical entities face challenges in improving the quality of care for patients, as well as reducing costs and increasing revenue. Efficient and effective entry of information into medical systems and EMRs may aid in the pursuit of these goals by increasing availability of data relevant to the care of patients.

BRIEF SUMMARY

By way of introduction, the preferred embodiments described below include methods, computer readable media, and systems for adaptively requesting and presenting medical information. Indication of a condition in an electronic medical record may be used to solicit input of additional information relevant to the indicated condition or multiple indicated conditions. In this way, a singular integrated or consolidated form may be presented to a user rather than requiring entry of the same information into different forms.

In a first aspect, medical data may be collected using an electronic medical documentation system coupled with a collection of Electronic Medical Records (EMRs) for patients of a medical entity, as well as other sources and repositories of medical data. An analysis may be triggered in response to information input into an EMR of a patient. A potential condition for the patient may be determined based on the analysis. Additional information indicated as relevant to the potential condition of the patient may be identified. A request for the identified additional information may be generated.

In a second aspect, a system is presented for adaptive medical data collection. The system may involve at least one memory operable to store EMRs and other medical data relating to conditions of patients of a medical facility. The system may also involve a processor configured to trigger an analysis of electronic records in response to information input into an EMR of a patient, identify additional information indicated as relevant to the potential condition of the patient from the other medical data, and generate a request for the identified additional information.

In a third aspect, a non-transitory computer readable storage medium has stored therein data representing instructions executable by a programmed processor for adaptive medical data collection. The storage medium includes instructions for triggering a probabilistic network analysis of electronic records in response to information input into an Electronic Medical Record (EMR) of a patient, determining a potential condition for the patient based on the probabilistic analysis, identifying additional information indicated as relevant to the potential condition of the patient, generating a request for the identified additional information, receiving at least a portion of the identified additional information, re-performing the probabilistic network analysis of electronic records using the received at least a portion of the identified additional information to update at least one probability of the probabilistic network.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Figure 1:
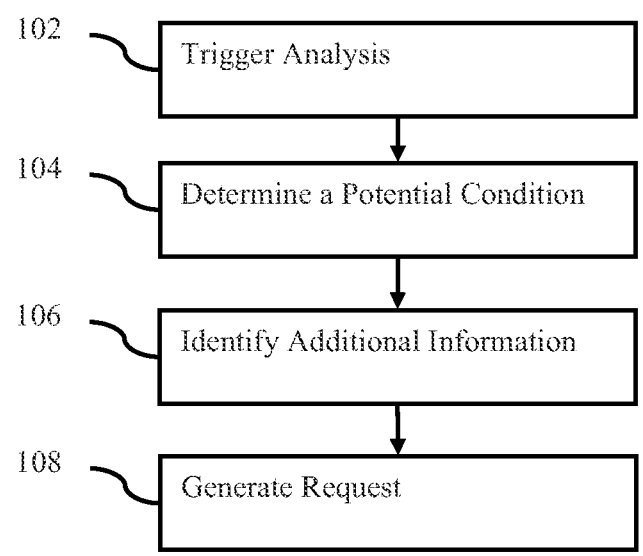
FIG. 1 is a flow chart diagram of one embodiment of a method for adaptive medical data collection.

The collection of medical data for a patient may adapt to information input into an electronic medical record (EMR) of a patient. The collection adapts based on inferences and conclusions that can be made using existing knowledge of the patient and other clinical information sources. Information currently being input may be combined with prior patient information and the other clinical information sources to suggest information related to a patient pertinent to current patient medical conditions. For example, previous patients having data similar to a current patient may be associated based on a distance metric relating to data of the current and previous patients. Data pertaining to associated previous patients may provide inferences and conclusions related to the current patient. The inferences and conclusions indicate suggested information specific to the current patient. A request for the suggested information specific to the patient may be made. The suggested information may further aid in the diagnosis or treatment of the patient. The suggested information may also be information related to a specific diagnosis or treatment determined to be relevant to a patient.

Adaptive medical information intake may take the form of a clinical documentation system. The clinical documentation system may be able to merge predefined form sections or templates such that information requests and presentation is not duplicated. Information being provided in real-time by a user and patient information extracted or accessed from previous patient EMRs may be used to determine which templates, or what parts of templates, are to be presented. The end result may be a real-time adaptable form constructed of templates, or template sections, specifically selected to suit a particular patient such that the constructed form contains all the relevant information needed to document the medical care of the patient. Adaptive medical information intake may also involve adapting to a user type or role by providing specific information related to specific roles of users accessing a clinical documentation system. For example, a nurse may be presented with different information than a physician. Physicians, nurses, and patients may be associated with different types of form sections and templates, containing specialized information relating to the role of the user.

A clinical documentation system may be configured to react to user input with suggestions that are sensitive to contexts specific to the patient. For example, causes of shortness of breath in an elderly patient may be provided based on information identified from an EMR for the patient. The contexts involved would indicate that causes of shortness of breath in a child would not apply because of an age identified for the patient. Similarly, an elderly patient presenting a problem of back pain may cause a clinical documentations system to prompt a user to ask four selected questions relevant to elderly patients amongst a total of 16-20 risk assessment questions relating to back pain for all possible types of patients.

A clinical documentation system may rely on prior clinical knowledge to support context sensitive suggestions for integrations of sections into a form. The different sources of prior knowledge may include ontologies to describe arbitrary contexts, clinical information and practice settings, clinical guidelines and workflows, prior patient EMRs, or any other source of clinical knowledge that may be useful in determining inferences for form assembly and creation. The use of both general and site-specific prior knowledge and information in a clinical documentation system increases the ability of the system to adapt and customize functionality for different users and different medical facilities.

In an embodiment two combined graphical models may be used in a clinical documentation system. The first graphical model may infer new sections to be added to a medical form document given a set of medical terms determined from an EMR of a patient. Another graphical model may infer new relevant medical terms or concepts associated with sections for a form of a clinical documentation system. The two models may also be modeled as a singular unified graphical model.

In an embodiment, a document model, a mapping model, and a domain model may be used. The document model outlines the structure a document may take. For example, multiple forms, form sections, subsections, elements, or questions may have rules associated with their respective presentation, content, and structure, and a document model may contain and enforce those rules. The domain model may be operable to link terms or concepts with other terms and concepts. The mapping model may be operable to link particular terms and concepts with the document model. For example, a weighted probabilistic network model may indicate links between specific terms and document elements such as form sections. The whole of the weighted probabilistic model may contain all possible connections between terms and form sections. When data is input into the three model system, inferences may be made using the three model system such that iterative analysis of input data may present acceptable levels of probability that proper form sections are included. For example, data including an age and gender may be input. Some connections in probabilistic network may be reduced to zero probability, or dropped, based on the data. In this example, the entry of Male may reduce the probability the patient is pregnant to 0%, and thus no sections relating to pregnancy will be included in a final document or form. As indicated above, as more data is input into the system, the process may work iteratively based on the additional data. In this example, the patient may be requested for an age, and provide information indicating that the patient is 10 years old, which in turn may reduce other probabilities in the model such as the probability the patient has Alzheimer's disease. The combined data may also be used to cumulatively reduce probabilities. In this example, the information indicating the patient is male may reduce the probability of the patient have breast cancer to 20%, and the information indicating the patient is 10 years old may further reduce the probability connection of the patient to breast cancer to 2%. Also, the domain model may analyze the input information to find associated information to provide the probabilistic network model to further update the probability connections. The iterative nature of providing and requesting information may continue until all probabilities are found acceptable, or found to be stable such that the entry of further information may not significantly affect the probabilities of the model. When a model reaches a steady probability state, a final document having form sections related to the remaining probable connections may be produced based on the rules of the document model. In an embodiment, the process may be continually iterative, and update probabilities and/or request further information continually as new information is input.

In an embodiment, a clinical documentation system may start with an initial user, which may be a medical practitioner or a patient, inputting data into a record. The data may be related to a presenting problem of a patient. The data may be as simple as a gender, age, or chief complaint. A set of relevant medical terms or concepts may be extracted from a record or group of records and fed as evidence to a first graphical model. The first graphical model may then output the most probable sections that may be included in a final form document given the set of relevant medical terms. Once information is provided for the most probable sections, a set of new relevant medical terms or concepts may be inferred by the second graphical model. The new set of relevant medical terms may be included with the initial set of relevant terms for use by the first model. Form sections may be generated all at once, or as determined applicable in real-time. If the document contains adequate sections based on predefined criteria, a final form document is produced. Also, in an embodiment, the document may be continually updated with new sections as new probable sections are identified based on input data.

FIG. 1 shows a flow chart diagram of an embodiment of a method for adaptive medical data collection. The method is implemented by a computerized physician order entry (CPOE) system, an automated workflow system, a review station, a workstation, a computer, a picture archiving and communication system (PACS) station, a server, combinations thereof, or other system in a medical facility. For example, the system or computer readable media shown in FIG. 3 implements the method, but other systems may be used.

Additional, different, or fewer acts may be performed. For example, an act for optimizing performance of a task of a workflow is provided. The method is implemented in the order shown or a different order. For example, acts 102, 104, 106, and 108 may be performed in parallel or repeated.

In act 102, an analysis of electronic records is triggered in response to information input into an EMR of a patient. The information may be input into electronic format through any method. In an embodiment, the information may be input into an electronic form of an EMR for a patient. In another embodiment, the information may be freely input into a generic EMR. For example, a user may speak into a microphone indicating a symptom. The patient may input the language "I have a headache" into the microphone where it is electronically transcribed to indicate a symptom. Any automated speech recognition method, such as Hidden Markov Models, Dynamic Time Warping, or Neural Networks, may be used.

The analysis may be triggered by any act. In an embodiment, the analysis is triggered based on recognition of an input of data into an EMR. Recognition of an updated field in an electronic form or database of an EMR of a patient may also trigger the analysis. The analysis may be performed using the information input into the EMR that triggered the analysis.

The electronic records may be any electronic record from which a potential diagnosis or treatment for a patient may be inferred independently, or in combination with other electronic records. For example, electronic records may include ontologies of arbitrary contexts, clinical data records, practice data records, clinical guidelines, EMRs of prior patients of a medical entity.

In act 104, a potential condition for the patient is determined based on the analysis. The analysis may be any analysis of electronic records capable of determining a potential condition for a patient. In an embodiment, the analysis involves the application of a machine learned model to the electronic records. For example, a Bayesian Network model trained using a Markov Chain Monte Carlo (MCMC) method may be used. In another example, an Expectation Maximization method based model may be used. The machine learned model may be trained using knowledge of an expert, or documented prior knowledge such as ontologies or medical databases. The model relates possible inputs as a feature vector for a patient to conditions.

A condition may involve any condition for a patient. In an embodiment, a determined condition involves a medical condition of the patient. For example, a condition may be heart disease, diabetes, epilepsy, hepatitis B, an allergy, or any condition related to the health or status of a patient. The condition is a possible diagnosis. A given input feature vector may indicate only one or more than one possible diagnoses and corresponding conditions.

In an embodiment, a probability that a patient has a condition is determined. The determined probability may be compared to a probability threshold, and if the probability meets a threshold it is determined that the condition applies to a patient. For example, a probability threshold may be 75% probability that a condition applies to a patient. Any determined probability larger than 75% may indicate that the condition applies to a patient. Any probability scoring system may be used. The machine learnt model may be probabilistic, so outputs a probability associated with one or more conditions.

In an embodiment, a probabilistic network may be used to determine possible conditions for a patient. The probabilistic network may have connections between terms or concepts and associated conditions represented by probabilities indicating that a current patient may have a condition. The probabilities may represent a current state of knowledge or data for a patient, and may be updated with inputs of additional information.

Multiple conditions may be determined to apply to a patient. A given model may provide more than one condition. Alternatively, different models, such as models specific to one or more conditions are applied to the data for the patient. Different models test for different conditions.

In act 106, additional information indicated as relevant to the potential condition of the patient is identified. The additional information may be associated with a condition determined for a patient, and identified upon determining that a condition applies to a patient. The additional information may involve any information relevant to determine a diagnosis for a patient. In an embodiment, the information may be determined to provide further indication that a condition applies to a patient. For example, if a patient indicates that they have a headache, other information such as history of headaches or recent physical injuries may be identified as relevant to a potential condition of persistent migraines, or post-concussion syndrome may be determined as potential conditions for a patient. All possible additional information may be stored in a collection, and relevant information may be identified from the collection. Additional information may be indicated as relevant through the application of a model, such as a machine learned graphical probabilistic model, as described herein.

Information may be configured as individual fields in a database associated with conditions, or collections of fields associated with conditions. When a condition is determined, or a possible condition is identified, fields associated with the condition may be identified. For example, a possible condition may be indicated with a probability of 73%, and all fields associated with the condition may be identified. Contrarily, if a probability of a condition is below a certain probability, such as below 35%, the fields associated with the condition may not be selected.

In an embodiment, additional information may be grouped as related to various conditions. For example, fields for the additional information may be assembled or contained in preformatted form templates. The form templates may each be associated with at least one condition. Once a condition is indicated, an associated form template may be identified. Multiple form templates may also be identified.

In an embodiment, additional information may be identified as individual fields for the additional information, wherein the individual fields are associated with a condition. All fields determined to be associated with a condition above a certain probability may be identified.

In act 108, a request for the identified additional information is generated. The request may involve selecting an established collection of information associated with the determined potential condition of the patient.

In an embodiment, the established collection of information is a preformatted medical form or form section. The form is electronic and may be a collection of fields associated with an EMR of a patient. The fields may be used to record and store the information associated with a condition. The fields may be clear of data, and configured for inputting information into an EMR, or other database. In an embodiment, the fields may have standardized information contained in them relating to a condition. For example, the standardized information may indicate that a certain dosage of acetaminophen is a typical treatment for a patient with a headache condition.

In an embodiment, some of the fields may be pre-populated with information for the patient pulled or mined from other portions of the EMR. For example, an age of the patient may be determined from other areas or individual records of an EMR, and the age may be pre-populated in the form. In another embodiment, the fields having information mined from an EMR will be withheld from presentation with the form. The information, however, may still be noted and associated with the condition for the patient. For example, a form may not indicate an age for a patient, but an age is determined, and a dosage for a medication may be determined based on the condition and the mined age of the patient. Any data mining may be used, such as is disclosed in U.S. Pat. No. 7,617,078, the disclosure of which is incorporated herein by reference.

In an embodiment, a collection of form templates or sections may be stored, each associated with a particular condition and containing fields for information relating to the condition. Form templates relating to conditions determined for a patient may be selected and presented on a display as part of generating a request for identified information relating to the conditions. The form templates may be presented in a pre-formatted whole, containing fields for all identified information relating to a condition. The form templates may also be presented in part, displaying only fields relating to information identified as most critical to diagnosis or treatment of the condition.

Multiple form templates for different conditions may be displayed at once as a singular form, or separately. If different forms include requests for the same information, the forms may be merged to provide one request rather than duplicative entry.

In an embodiment, condition determination may be iterative. A portion of the identified additional information may be received. Other information regarding the potential condition of the patient may be identified based on the received identified additional information. The analysis may be re-performed using the other information to identify further information relevant to the potential condition of the patient, and a second request for the further information may be generated. Numerous inputs of information and requests may be generated during an iterative process of adaptive medical information input to determine a diagnosis or treatment of a condition.

In an embodiment involving machine learned models, the performing and re-performing an analysis may be undertaken by applying a first machine learned model and the identifying other information may involve the application of a second machine learned model. The second machine learned model may receive the identified additional information and generate the other information. The other information may be additional terms or medical characteristics that may be added to the analysis of the first machine learned model to provide higher accuracy for determining information, or forms, pertinent to the patient. As such, there may exist a form hierarchy wherein a general condition, such as head pain, has a general form template designed to gather further information to further diagnose and narrow the head pain condition. For example, the request for information may involve a query for information to determine if a patient has a concussion, or if the patient suffers from chronic migraines, each of which may have respective forms in the hierarchy, with fields for specific information relating to each condition. The second machine learned model may be designed to take the input from the initial request, and combine the information with other information to further output a potential diagnosis for a condition that may be input into the first model to identify further forms.

Figure 2:
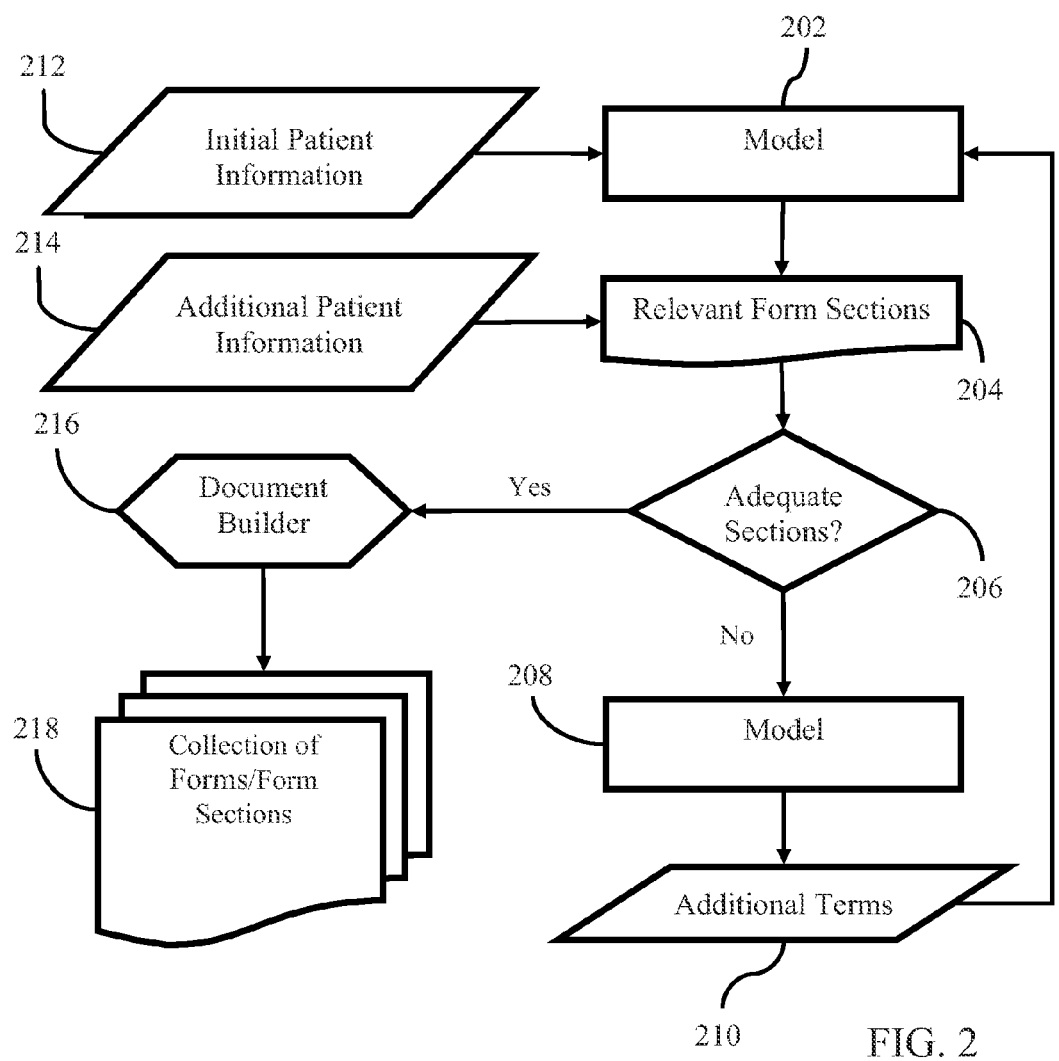
FIG. 2 is a flow chart diagram of another embodiment of a method for adaptive medical data collection.

FIG. 2 shows a flow chart diagram of an embodiment of adaptive medical data collection. The diagram may describe the operation of a system, such as that described with respect to FIG. 3 below, or another structure operably consistent with the diagramed components.

An analysis of electronic records using a model 202 may be triggered in response to information 212 input into an EMR of a patient. The model 202 may determine a potential condition for the patient based on the analysis. The model 202 may identify additional information contained in form sections 204 indicated as relevant to the potential condition of the patient. A request for the identified additional information may be generated by selecting a medical form or form section 204. The form or form section 204 may be determined relevant and selected based on a probability a patient has a condition associated with the form determined by the model 202. Form sections 204 may be entire forms, or sections of forms designated for certain conditions. The relevant form sections 204 may be displayed for data presentation or data input.

Adaptive medical data collection may be iterative. An iterative embodiment may involve receiving at least a portion of the identified information. For example, additional patient information 214 may be input into some, or all, of the fields of relevant form sections 204. Using a second model 208, other information or additional terms 210 may be identified or determined regarding a potential condition of a patient based on the received identified information. The analysis may be re-performed by a first model 202 using the additional terms 210 to identify further relevant form sections 204.

Iterations may continue until is determined in act 206 that there is enough, or adequate, requested or presented information, or whether there have been adequate form sections identified, generated, and/or presented. The determination may be made based on predefined criteria. In an embodiment, a minimum number of form sections may be required. In an embodiment, an adequate section determination 206 may be made based on probabilities of a condition for a patient. For example, form templates associated with conditions determined beyond a threshold may be provided. Further, conditions within a range of probabilities may require iterations to better establish a likelihood the patient has the condition. The model 208 may refine the information contained by providing additional terms to use with the model 202 to select further relevant form sections 204. For example, iterations may be provided for conditions determined with a probability of 45% to 75%, where 75% may be the probability threshold. Iterations may continue until all probabilities determined for all conditions are either below 45%, or above 75%.

In an embodiment, when it is determined that there are adequate form sections, a document builder 216 may be used to create a total collection of forms/form sections for generation or presentation. The document builder 216 may also be included in a non-iterative embodiment, after relevant form sections 204 have been determined by the model 202. The collection of form sections 218 may be presented in an order according to a set of ordering or ranking rules. In an embodiment, form sections may be ranked by probability of a patient having the condition associated with the form section, with the highest probabilities being placed most prominently in a collection of form sections 218. Examples of prominent placements of form sections 204 may include being placed at the top of a collection 218, displayed with highlighted or more noticeable text than other form sections of the collection 218, or a form section may require input prior to inputs of other sections.

In an embodiment, the models 202 and 208 may be one unified model. In an embodiment, the models may be machine learning models. The models 202 and 208 may be trained based on a collection of prior medical knowledge to represent and efficiently manipulate a probability distribution of conditions for a patient associated with document sections 206. Document sections 206 associated with a condition determined to a certain probability to apply to a patient may be included in a personalized main document 218. The main document 218 may group relevant subsections 206 that contain information needed to be registered for a given patient in a given clinical visit. The relevant subsections 206 included in a main document 218 are associated with conditions having a probability of relating to a patient. The probability of relating to a patient may be modeled using the machine learned model 202, which may be a generative probabilistic model such as a Bayesian Network model. The generative probabilistic model may represent relationships among medical concepts or terms and document sections such as term-term relations, sections-term relations, sections-terms relations, and section-section relations.

Probabilistic graphical models are graph-based representations for encoding a distribution over multi-dimensional space, wherein each node in a graph represents a random variable. Links between nodes specify a direction or relevance of an association. The edges of the graph each have an associated real number usually referred to as an exponential family weight. A positive link weight between two nodes means that an increase or decrease in the value of node 1 causes an increase or decrease, respectively, in a value for linked node 2. A negative link weight indicates a decrease value for node 1 increases the value for node 2 or vise versa. The absolute value of the weights is a measure of strength of influence by any parent node on a child, or linked, node. A node in a graphical model may encode either discrete or continuous probability distributions.

Graphical models for adaptive medical information input may be trained in two steps. The first step involves learning or designing the structure of the network. The first step may be performed by an expert in the knowledge of the medical area and form constructs being graphed, by a prior form knowledge structure, or automatically through a learning algorithm such as a Markov Chain Monte Carlo (MCMC) local search method. For example, an expert may recognize that a particular form may be associated with a particular condition. An expert may also recognize that the information in one form is related to information in another form. These associations may be recorded and integrated to form the structure of the network. The first step may also involve a hybrid creation which may consist of applying an automatic algorithm first and later modifying the resulting network using known relations, an expert, or prior knowledge.

A second step in training a graphical model for adaptive medical information input may involve learning the parameters of a network including unrealized relationships between conditions and forms, or strength of associations between forms and conditions. In an embodiment, an Expectation Maximization search algorithm may be used. Such an embodiment may alternate between solving two problems, an expectation and a maximization, to compute maximum likelihood estimates of parameters for the model. The algorithm may start with random initializations of model parameters, and converge onto optimal point estimates, resulting in a network of nodes relating to conditions and associated form sections.

Once a model is trained, a set of evidences may indicate a probability that a given section should be included in a current personalized collection of forms 218. The evidences may include information such as patient characteristics, complaints, or sections already included in a document. Probabilities may be determined by a model using any method. In an embodiment, a Junction Tree algorithm is used.

Figure 3:
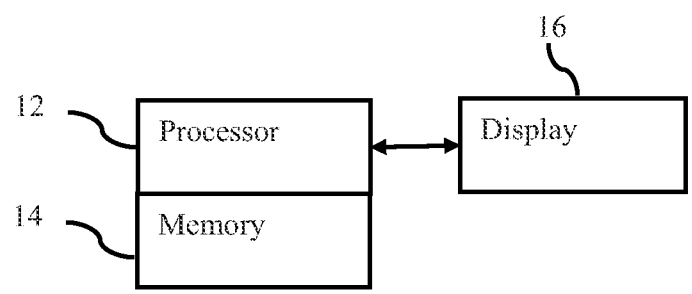
FIG. 3 is a block diagram of one embodiment of a system for adaptive medical data collection.

FIG. 3 shows a system for adaptive medical data collection. The system is a server, network, workstation, computer, database, or combinations thereof. The system 10 includes a processor 12, a memory 14, and a display 16. Additional, different, or fewer components may be provided. For example, the system includes a scanner, a network connection, a wireless transceiver or other device for receiving patient information and/or communicating patient information to other systems.

The memory 14 is a buffer, cache, RAM, removable media, hard drive, magnetic, optical, database, or other now known or later developed memory. The memory 14 is a single device or group of two or more devices. The memory 14 is shown within the system, but may be outside or remote from other components of the system, such as a database or PACS memory.

The memory 14 stores EMRs for patients and other medical data relating to conditions of patients of a medical facility. Models, such as probabilistic graphical models trained using medical data may also be stored on the memory 14. Multiple EMRs of other patients may also be stored on the memory 14. In an embodiment, the memory 14 is operable to store a plurality of electronic medical records of a plurality of patients of a medical entity, specific electronic medical record of a patient as well as ontologies, electronic clinical information, practice settings, machine logs, clinical guidelines, and workflows.

The memory 14 is additionally or alternatively a non-transitory computer readable storage medium with processing instructions. The memory 14 stores data representing instructions executable by the programmed processor 12 for adaptive medical information input. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

In an embodiment, the instructions may include triggering a probabilistic network analysis of electronic records in response to information input into an Electronic Medical Record (EMR) of a patient, determining a potential condition for the patient based on the probabilistic analysis, identifying additional information indicated as relevant to the potential condition of the patient, generating a request for the identified additional information, receiving at least a portion of the identified additional information, and re-performing the probabilistic network analysis of electronic records using the received at least a portion of the identified additional information to update at least one probability of the probabilistic network.

The processor 12 is a server, general processor, digital signal processor, graphics processing unit, application specific integrated circuit, field programmable gate array, digital circuit, analog circuit, combinations thereof, or other now known or later developed device for medical category determination. The processor 12 is a single device, a plurality of devices, or a network. For more than one device, parallel or sequential division of processing may be used. Different devices making up the processor 12 may perform different functions, such as a handwriting detector by one device and a separate device for communicating or processing the detected handwritten data. In one embodiment, the processor 12 is a control processor or other processor of a computerized data entry system for an EMR storage or database system. The processor 12 operates pursuant to stored instructions to perform various acts described herein.

The processor 12 is configured by software or hardware adaptive medical information input. The processor 12 may be configured to trigger an analysis of electronic records stored on the memory 14 in response to information input into an EMR of a patient. The processor 12 may further be configured to identify additional information indicated as relevant to the potential condition of the patient from the other medical data. The processor 12 may also be configured to generate a request for the identified additional information. The request may be presented on the display 16. A collection of requests may also be presented on the display 16.

The display 16 is a CRT, LCD, plasma, projector, printer, or other output device for showing an image. The display 16 displays a user interface with an image. The user interface may be for the entry of information, such as information that may be used for triggering an analysis of electronic records stored on the memory 14. The user interface may be for entering information into an EMR, or displaying a graphical model.

Figure 4:
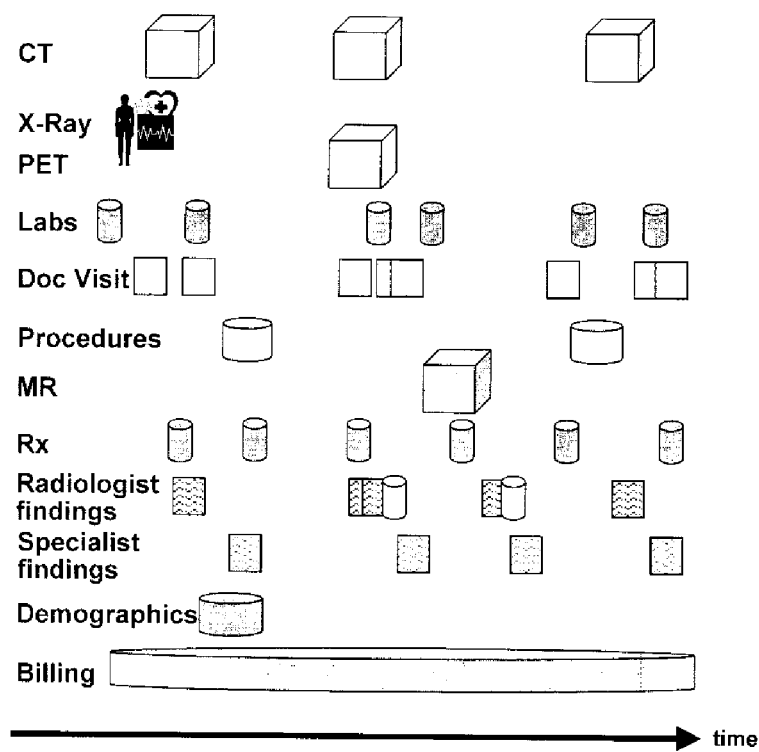
FIG. 4 is a representation of an electronic medical record.

FIG. 4 shows an exemplary EMR 200. Health care providers may employ automated techniques for information storage and retrieval. The use of an EMR to maintain patient information is one such example. As shown in FIG. 4, an exemplary EMR 200 includes information collected over the course of a patient's treatment or use of an institution. The information may be collected using forms, form templates, form sections, or combinations thereof. The information may include, for example, computed tomography (CT) images, X-ray images, laboratory test results, doctor progress notes, details about medical procedures, prescription drug information, radiological reports, other specialist reports, demographic information, family history, patient information, and billing (financial) information. Any of this information may provide for information related to a potential condition for a patient.

An EMR may include a plurality of data sources, each of which typically reflects a different aspect of a patient's care. Alternatively, the EMR is integrated into one data source. Structured data sources, such as financial, laboratory, and pharmacy databases, generally maintain patient information in database tables. Information may also be stored in unstructured data sources, such as, for example, free text, images, and waveforms. Often, characteristics, such as key clinical findings, are stored within unstructured physician reports, annotations on images or other unstructured data source.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A computerized method carried out by at least one server having at least one processor for adaptive medical data collection, the method comprising:
   triggering a probabilistic analysis of electronic records in response to a first set of information input into an Electronic Medical Record (EMR) of a patient;
   determining, with the at least one processor, a first potential condition for the patient based on the probabilistic analysis;
   identifying, with the at least one processor, a second set of information indicated as relevant to the first potential condition of the patient;
   generating, with the at least one processor, a first request for the second set of information by identifying an established collection of information associated with the first potential condition of the patient and providing the first request for the second set of information in a preformatted medical form established for the collection of the second set of information, wherein the preformatted medical form is populated using the established collection of information associated with the first potential condition of the patient, and wherein the preformatted medical form is automatically adapted based on the first set of information input into the EMR;
   receiving at least a portion of the second set of information;
   repeating the triggering of the probabilistic analysis;
   re-performing, with the at least one processor, the probabilistic analysis using the second set of information to identify a second potential condition and a third set of information relevant to the second potential condition of the patient; and
   generating, with the at least one processor, a second request for the third set of information wherein the preformatted medical form is automatically adapted based on the second set of information received subsequent to the first request.

2. The method of claim 1, wherein triggering the analysis of the electronic records comprises triggering an analysis of ontologies of arbitrary contexts, clinical data records, practice data records, clinical guidelines, or EMRs of prior patients of a medical entity.

3. The method of claim 1, wherein triggering comprises recognizing an input of data into the EMR of the patient.

4. The method of claim 1, wherein triggering the analysis comprises triggering an application of a machine learned model to the electronic records.

5. The method of claim 4, wherein triggering the application of a machine learned model comprises a triggering an application of a Bayes Net model trained using a Markov Chain Monte Carlo (MCMC) method, and an Expectation Maximization method based model.

6. The method of claim 1, wherein determining the first potential condition for the patient comprises determining a probability the condition applies to the patient, and comparing the probability to a predetermined probability threshold.

7. The method of claim 1, wherein triggering the analysis comprises triggering an application of a first machine learned model to the electronic records, identifying other information regarding the first potential condition of the patient comprises applying a second machine learned model to the second set of information, and re-performing the analysis comprises applying the first machine learned model to the other information.

8. A system for adaptive medical data collection, the system comprising:
at least one memory operable to store Electronic Medical Records (EMRs) and other medical data relating to conditions of patients of a medical facility; and
a processor configured to:
trigger a probabilistic analysis of electronic records in response to a first set of information input into an EMR of a patient, the probabilistic analysis comprising a probabilistic network of associated terms derived from the other medical data;
determine a first potential condition for the patient based on the probabilistic analysis;
identify a second set of information indicated as relevant to the first potential condition of the patient from the probabilistic network; and
generate a first request for the second set of information by identifying an established collection of information associated with the first potential condition of the patient and providing the first request for the second set of information in a preformatted medical form established for the collection of the second set of information, wherein the preformatted medical form is populated using the established collection of information associated with the first potential condition of the patient, and wherein the preformatted medical form is automatically adapted based on the information input into the EMR and data input into the EMR subsequent to the generation of the first request;
receive at least a portion of the second set of information;
repeat the triggering of the probabilistic analysis;
re-perform the probabilistic analysis using the second set of information to identify a second potential condition and a third set of information relevant to the second potential condition of the patient; and
generate a second request for the third set of information wherein the preformatted medical form is automatically adapted based on at least a portion of the second set of information received subsequent to the first request.

9. The system of claim 8, wherein the other medical data comprises ontologies of arbitrary contexts, clinical data records, practice data records, clinical guidelines, or EMRs of prior patients of a medical entity.

10. The system of claim 8, wherein the analysis is triggered by a recognition of data input into the EMR of the patient.

11. The system of claim 8, wherein the analysis comprises the application of a machine learned model.

12. The system of claim 11, wherein the machine learned model comprises a generative probabilistic model.

13. A non-transitory computer readable storage medium having stored therein data representing instructions executable by a programmed processor for adaptive medical data collection, the storage medium comprising instructions for:
triggering a probabilistic network analysis of electronic records in response to information input into an Electronic Medical Record (EMR) of a patient;
determining a first potential condition for the patient based on the probabilistic analysis;
identifying a second set of information indicated as relevant to the first potential condition of the patient;
generating a request for the second set of information by selecting an established collection of information associated with the first potential condition of the patient and providing the first request for the second set of information in a preformatted medical form established for the collection of the second set of information, wherein the preformatted medical form is populated using the established collection of information associated with the first potential condition of the patient, and wherein the preformatted medical form is automatically adapted based on the first set of information input into the EMR;
receiving at least a portion of the second set of information;
repeating the triggering of the analysis;
re-performing the probabilistic network analysis of electronic records using the at least the portion of the second set of information to update at least one probability of the probabilistic network and to identify a third set of information relevant to a second potential condition of the patient; and
generating, a second request for the third set of information wherein the preformatted medical form is automatically adapted based on at least a portion of the second set of information received subsequent to the first request.

14. The medium of claim 13, wherein when adequate information is not available the instructions further comprise:
identifying a fourth set of information regarding the potential condition of the patient based on the third set of information;
updating at least one probability of the probabilistic network; and
generating a second request for the further information based on the updated probability.

15. The medium of claim 13, wherein the instructions further comprise performing the instructions iteratively until it is determined that adequate information has been requested such that each probability of the probabilistic network is either below a first threshold or above a second threshold.

16. The medium of claim 13, wherein information is requested using electronic forms.

17. The medium of claim 13, wherein triggering comprises recognizing an input of data into the EMR of the patient.

\* \* \* \* \*